US006127363A

United States Patent [19]
Doherty, Jr. et al.

[11] Patent Number: 6,127,363
[45] Date of Patent: Oct. 3, 2000

[54] LOCAL ADMINISTRATION OF TYPE IV PHOSPHODIESTERASE INHIBITORS FOR THE TREATMENT OF ERECTILE DYSFUNCTION

[75] Inventors: Paul C. Doherty, Jr., Cupertino, Calif.; Virgil A. Place, Kawaihae, Hi.; William L. Smith, Montclair, N.J.

[73] Assignee: Vivus, Inc., Mountain View, Calif.

[21] Appl. No.: 09/437,999

[22] Filed: Nov. 10, 1999

Related U.S. Application Data

[63] Continuation-in-part of application No. 09/181,070, Oct. 27, 1998, Pat. No. 6,037,346, which is a continuation-in-part of application No. 08/958,816, Oct. 28, 1997, abandoned.

[51] Int. Cl.[7] ................................................. A61K 31/55
[52] U.S. Cl. .......................... 514/220; 514/263; 514/274; 514/253; 514/245; 514/303; 514/390; 514/357; 514/277; 514/332; 514/334; 514/337; 514/339; 514/276.7; 514/280.4; 514/284.1
[58] Field of Search ..................................... 514/263, 274, 514/220, 253, 245, 303, 390, 357, 277, 332, 334, 337, 339, 276.7, 284.4, 284.1

[56] References Cited

U.S. PATENT DOCUMENTS

| | | |
|---|---|---|
| 3,819,631 | 6/1974 | Broughton et al. . |
| 3,933,822 | 1/1976 | Broughton et al. . |
| 4,039,544 | 8/1977 | Broughton et al. . |
| 4,666,908 | 5/1987 | Hamilton . |
| 4,801,587 | 1/1989 | Voss et al. . |

(List continued on next page.)

FOREIGN PATENT DOCUMENTS

| | | |
|---|---|---|
| WO 94/28902 | 12/1994 | WIPO . |
| WO 96/16644 | 6/1996 | WIPO . |

OTHER PUBLICATIONS

Bush et al. (1992), "Nitric Oxide is a Potent Relaxant of Human and Rabbit Corpus Cavernosum," *The Journal of Urology* 147: 1650–1655.

Doherty (1997), "Oral, Transdermal, and Transurethral Therapies for Erectile Dysfunction," *Male Infertility and Dysfunction*, Springer–Verlag New York, Inc., pp. 452–467.

Rajfer et al. (1992), "Nitric Oxide as a Mediator of Relaxation of the Corpus Cavernosum in Reponse to Nonadrenergic, Noncholinergic Neurotransmission," *The New England Journal of Medicine* 326(2):90–94.

Taher et al. (1992), "Cyclic Nucleotide Phosphodiesterase Activity in Human Cavernous Smooth Muscle and the Effect of Various Selective Inhibitors," *International Journal of Impotence Research, Basic and Clinical Studies* 4(2):11.

Trigo–Rocha et al. (1993), "The Role of Cyclic Adenosine Monophosphate, Cyclic Guanosine Monophosphate, Endothelium and Nonadrenergic, Noncholinergic Neurotransmission in Canine Penile Erection," *The Journal of Urology* 149:872–877.

Barnette et al. (1996), "Phosphodiesterase 4: Biological Underpinnings for the Design of Improved Inhibitors," *Pharmacology Reviews and Communications* 8:65–73.

Bivalacqua et al. (1999), "Potentiation of Erectile Response and cAMP Accumulation by Combination of Prostaglandin $E_1$ and Rolipram, a Selective Inhibitor of a Type 4 Phosphodiesterase (PDE 4)," *The Journal of Urology* 162:1–8.

Boolell et al. (1996), "Sildenafil: An Orally Active Type 5 Cyclic GMP–Specific Phosphodiesterase Inhibitor for the Treatment of Penil Erectile Dysfunction," *International Journal of Impotence Research* 8:47–52.

Burnouf et al. (1998), "Phosphodiesterases 4 Inhibitors," *Annual Reports in Medicinal Chemistry* 33:91–109.

Christensen et al. (1996), "Molecular Aspects of Inhibitor Interaction with PDE4," *Phosphodiesterase Inhibitors*, Academic Press, Harcourt Brace and Company, Publishers, pp. 185–207.

Doherty (1999), "Phosphodiesterase 4 Inhibitors as Novel Anti–Infammatory Agents," *Current Opin. Chem. Brol.* 3(4):466–473.

Martinez–Piñeiro et al. (1993), "Cyclic Guanosine Monophosphate Mediates Penile Erection in the Rat," *European Urology* 24:492–499.

McGarry et al. (1999), "Benzofuran Based PDE4 Inhibitors," *Bioorganic & Medicinal Chemistry* 7:1131–1139.

Müller et al. (1996), "Subtypes of the Type 4 cAMP Phosphodiesterases: Structure, Regulation and Selective Inhibition," *Trends Pharm. Sci.* 17(8):294–298.

Perrier et al. (1999), "Substituted Furans as Inhibitors of the PDE4 Enzyme," *Bioorganic & Medicinal Chemistry Letters* 9:323–326.

Polson et al. (1996), "Cyclic Nucleotide Phosphodieterases and Vascular Smooth Muscle," *Annu. Rev. Pharmacol. Toxicol.* 36:403–427.

Sparwasser et al. (1994), "Smooth Muscle Tone Regulation in Rabbit Cavernosal and Spongiosal Tissue by Cyclic AMP–and Cyclic GMP–Dependent Mechanisms," *The Journal of Urology* 152:2159–2163.

Stief et al. (1995), "Cyclic Nucleotide Phosphodieterase (PDE) Isoenzymes in Human Cavernous Smooth Muscle: Characterization and Functional Effects of PDE–Inhibitors in Vitro and In Vivo," *International Journal of Impotence Research, Basic and Clinical Studies* 7(1):6–7.

Taher et al. (1997), "Cyclic Nucleotide Phosphodieterase in Human Cavernous Smooth Muscle," *World Journal of Urology* 15:32–35.

Truss et al. (1998), "Phosphodiesterase Inhibitors in the Treatment of Erectile Dysfunction," *Drugs of Today* 34(9), summary only.

*Primary Examiner*—James H. Reamer
*Attorney, Agent, or Firm*—Dianne E. Reed; Reed & Associates

[57] ABSTRACT

A method is provided for treating erectile dysfunction, e.g., vasculogenic erectile dysfunction such as vasculogenic impotence. The method involves the administration of a Type IV phosphodiesterase inhibitor or a pharmaceutically acceptable salt, ester, amide or derivative thereof, wherein administration is local, i.e., transurethral, intracavernosal, topical or transdermal. A preferred mode of administration is transurethral. Pharmaceutical formulations and kits are provided as well.

106 Claims, 4 Drawing Sheets

U.S. PATENT DOCUMENTS

| | | |
|---|---|---|
| 5,145,852 | 9/1992 | Virag . |
| 5,242,391 | 9/1993 | Place et al. . |
| 5,250,534 | 10/1993 | Bell et al. . |
| 5,272,147 | 12/1993 | Bell et al. . |
| 5,346,901 | 9/1994 | Bell et al. . |
| 5,426,107 | 6/1995 | Bell et al. . |
| 5,506,347 | 4/1996 | Erion et al. . |

LOCAL ADMINISTRATION OF TYPE IV PHOSPHODIESTERASE INHIBITORS FOR THE TREATMENT OF ERECTILE DYSFUNCTION

CROSS-REFERENCE TO RELATED APPLICATIONS

This application is a continuation-in-part of U.S. Ser. No. 09/181,070, filed Oct. 27, 1998, now U.S. Pat. No. 6,037,346 which is a continuation-in-part of U.S. Ser. No. 08/958,816, filed Oct. 28, 1997, now abandoned.

TECHNICAL FIELD

This invention relates generally to methods and pharmaceutical compositions for treating erectile dysfunction; more particularly, the invention relates to local administration of Type IV phosphodiesterase inhibitors to treat erectile dysfunction.

BACKGROUND

Impotence is the consistent inability to achieve or sustain an erection of sufficient rigidity for sexual intercourse. It has recently been estimated that approximately 10 million American men are impotent (R. Shabsigh et al., "Evaluation of Erectile Impotence," *Urology* 32:83–90 (1988); W. L. Furlow, "Prevalence of Impotence in the United States," *Med. Aspects Hum. Sex.* 19:13–6 (1985)). Impotence is recognized to be an age-dependent disorder, with an incidence of 1.9 percent at 40 years of age and 25 percent at 65 years of age (A. C. Kinsey et al., "Age and Sexual Outlet," in *Sexual Behavior in the Human Male*; A. C. Kinsey et al., eds., Philadelphia, Pa.: W. B. Saunders, 218–262 (1948)). In 1985 in the United States, impotence accounted for more than several hundred thousand outpatient visits to physicians (National Center for Health Statistics, National Hospital Discharge Survey, 1985, Bethesda, Md., Department of Health and Human Services, 1989 DHHS publication no. 87-1751). Depending on the nature and cause of the problem, treatments include psychosexual therapy, hormonal therapy, administration of vasodilators such as nitroglycerin and α-adrenergic blocking agents ("α-blockers"), oral administration of other pharmaceutical agents, vascular surgery, implanted penile prostheses, vacuum constriction devices and external aids such as penile splints to support the penis or penile constricting rings to alter the flow of blood through the penis.

A number of causes of impotence have been identified, including vasculogenic, neurogenic, endocrinologic and psychogenic. Vasculogenic impotence, which is caused by alterations in the flow of blood to and from the penis, is thought to be the most frequent organic cause of impotence. Common risk factors for vasculogenic impotence include hypertension, diabetes, cigarette smoking, pelvic trauma, and the like. Neurogenic impotence is associated with spinal-cord injury, multiple sclerosis, peripheral neuropathy caused by diabetes or alcoholism and severance of the autonomic nerve supply to the penis consequent to prostate surgery. Erectile dysfunction is also associated with disturbances in endocrine function resulting in low circulating testosterone levels and elevated prolactin levels.

Impotence can also be a side effect of various classes of drugs, in particular, those that interfere with central neuroendocrine control or local neurovascular control of penile smooth muscle. Krane et al., *New England Journal of Medicine* 321:1648 (1989). Penile erection requires (1) dilation of the arteries that regulate blood flow to the lacunae of the corpora cavernosum, (2) relaxation of trabecular smooth muscle, which facilitates engorgement of the penis with blood, and (3) compression of the venules by the expanding trabecular walls to decrease venous outflow.

Trabecular smooth muscle tone is controlled locally by adrenergic (constrictor), cholinergic (dilator) and nonadrenergic, noncholinergic (dilator) innervation, and by endothelium-derived vasoactive substances such as vasoactive intestinal polypeptide (VIP), prostanoids, endothelin and nitric oxide. High sympathetic tone (noradrenergic) is implicated in erectile dysfunction, and, in some patients, the disorder can be successfully treated with noradrenergic receptor antagonists. See, e.g., Krane et al., supra.

There is also evidence that dopaminergic mechanisms are involved in erectile function. For example, pharmacologic agents that elevate the level of brain dopamine or stimulate brain dopamine receptors increase sexual activity in animals (see, e.g., Gessa & Tagliamonte, *Life Sciences* 14:425 (1974); Da Prada et al., *Brain Research* 57:383 (1973)).

Administration of L-DOPA, a dopamine precursor, enhances sexual activity in male rats. L-DOPA has been used in the treatment of Parkinsonism and is known to act as an aphrodisiac in some patients (Gessa & Tagliamonte, supra; Hyppa et al., *Acta Neurologic Scand.* 46:223 (Supp. 43, 1970)). Specific dopamine agonists have been studied for their effects on erectile function. Apomorphine, (n-propyl) norapo-morphine, bromocryptine, amantidine, fenfluramine, L-DOPA and various other pharmacological activators of central dopaminergic receptors have been found to increase episodes of penile erection in male rats (Benassi-Benelli et al., *Arch. int. Pharmacodyn.* 242:241 (1979); Poggioli et al., *Riv. di Farm. & Terap.* 9:213 (1978); Falaschi et al., *Apomorphine and Other Dopaminomimetics*, 1:117–121 (Gessa & Corsini, Eds., Raven Press, N.Y.)). In addition, U.S. Pat. No. 4,521,421 to Foreman relates to the oral or intravenous administration of quinoline compounds to treat sexual dysfunction in mammals.

The currently available dopamine agonists, with few exceptions, have found limited use in the treatment of erectile dysfunction because of their peripheral side effects. These effects include nausea and vomiting, postural hypotension, arrhythmias, tachycardia, dysphoria, psychosis, hallucinations, drowsiness and dyskinesias (See, e.g., Martindale *The Extra Pharmacopoeia*, 31st Ed., pages 1151–1168).

Other pharmaceutical methods for treating erectile dysfunction have also proved to be problematic. For example, with Viagra®, the most recently introduced oral drug therapy, not only have significant side effects been encountered, but interaction with other systemically administered medications has posed enormous risks and numerous fatalities have in fact been reported.

The invention described herein provides a means to avoid the above-mentioned problems encountered with the systemic administration of pharmacologically active agents to treat erectile dysfunction. Specifically, the invention relates to methods and formulations for effectively treating erectile dysfunction by locally administering a selected active agent, wherein the active agent is an inhibitor of a phosphodiesterase.

Phosphodiesterases (PDEs) are a class of intracellular enzymes involved in the metabolism of the second messenger nucleotides, cyclic adenosine monophosphate (cAMP), and cyclic guanosine monophosphate (cGMP) (see, e.g., Doherty, "Oral, Transdermal and Transurethral Therapies for Erectile Dysfunction" in *Male Infertility and Dysfunction*, Helistrom, ed., Chapter 34 (New York, N.Y.: Springer-Verlag, 1997)). Numerous phosphodiesterase inhibitors have previously been described in the literature for a variety of therapeutic uses, including treatment of obstructive lung disease, allergies, hypertension, angina, congestive heart failure and depression (see, e.g., Goodman and Gilman's *The Pharmacological Basis of Therapeutic* Ninth Edition, Chapter 34). Oral and parenteral administration of phosphodiesterase inhibitors, as alluded to above, have also been suggested for the treatment of erectile dysfunction (Doherty, supra; see also PCT Publication Nos. WO 96/16644 and WO 94/28902).

As explained by Komas et al. in *Phosphodiesterase Inhibitors*, Eds. Schudt et al., Ch. 6 (San Diego, Calif.: Academic Press, 1996), those initially working in the field partially purified what was believed to be a single enzyme responsible for specifically hydrolyzing the 3'-bond of cyclic nucleotides. However, it later became clear that multiple forms of phosphodiesterase inhibitors were present in different tissues; the enzymes were classified into three major groups, one of which exhibited high affinity for cAMP and designated as the "low $K_m$" cAMP PDE. This "low $K_m$" cAMP PDE was ultimately discovered to consist of two distinct isoenzymes having entirely different properties, including physical properties, kinetic characteristics and inhibitor specificities. One isoenzyme was found to be very sensitive to inhibition by cilostamide and cGMP, and is now known as the cAMP-specific, cGMP-inhibited cyclic nucleotide phosphodiesterase (cGI-PDE) or PDE III. The second isoenzyme was found to be unaffected by cGMP but inhibited by the alkoxybenzyl-substituted imidazoline RO20-1724, and has been classified as "PDE IV." Komas et al., supra.

With the possible exception of platelets, Type IV PDE is present in cell types associated with allergic and inflammatory diseases. Several Type IV PDE inhibitors have been developed with the goal of producing effective anti-inflammatory agents. For the most part, these inhibitors fall into three broad groups: xanthines; rolipram analogues; and quinazolinediones. Applicants are not, however, aware of any art that teaches or discloses the local administration of Type IV phosphodiesterase inhibitors in the treatment of erectile dysfunction.

The phosphodiesterases have now been classified into ten major families, Types I–X, based on amino acid or DNA sequences. The members of the family vary in their tissue, cellular and subcellular distribution, as well as their links to cAMP and cGMP pathways. For example, the corpora cavernosa contains: Type III phosphodiesterases, which are cAMP-specific cGMP inhibitable; Type IV phosphodiesterases, which as explained above are the high affinity, high-specificity cAMP-specific form; and type V phosphodiesterases, one of the cGMP-specific forms.

The following documents are of interest insofar as they relate to the treatment of erectile dysfunction by delivering pharmacologically active agents locally to the penis:

U.S. Pat. No. 4,127,118 to Latorre describes the injection of vasodilator drugs into the corpora cavernosa of the penis to dilate the arteries that supply blood to the erectile tissues, thereby inducing an erection;

U.S. Pat. No. 5,439,938 to Snyder et al. describes the administration of nitric oxide (NO) synthase inhibitors by direct injection of a drug into the corpora cavernosa, by topical drug administration or transurethral drug administration, for inhibiting penile erection due to priapism and for treating urinary incontinence;

Virag et al., *Angiology-Journal of Vascular Diseases* (February 1984), pp. 79–87, Brindley, *Brit. J. Psychiat.* 143:332–337 (1983) and Stief et al., *Urology* XXXI:483–485 (1988) respectively describe the intracavernosal injection of papaverine (a smooth muscle relaxant), phenoxybenzamine or phentolamine (α-receptor blockers) and a phentolamine-papaverine mixture to treat erectile dysfunction; and PCT Publication No. WO 91/16021, U.S. Pat. No. 4,801, 587 to Voss et al., and U.S. Pat. Nos. 5,242,391, 5,474,535, 5,686,093 and 5,773,020 to Place et al. relate to the treatment of erectile dysfunction by delivery of a vasoactive agent into the male urethra.

The invention, as noted above, is directed to local administration of pharmacologically active agents to treat erectile dysfunction. The agents are Type IV phosphodiesterase inhibitors. Surprisingly, it has now been found by the inventors herein that local administration of these phosphodiesterase inhibitors is highly effective in treating erectile dysfunction, e.g., vasculogenic impotence. Local administration of Type IV phosphodiesterase inhibitors, and transurethral administration in particular, generally enables use of a lower drug dosage, avoids many of the side effects encountered with other modes of administration, and avoids interaction with other systemically administered medications an individual may be taking. The local administration of Type IV phosphodiesterase inhibitors to treat erectile dysfunction accordingly represents an important advance in the treatment of impotence and other erectile disorders.

SUMMARY OF THE INVENTION

It is a primary object of the invention to address the above-described need in the art by providing a novel method for treating erectile dysfunction by locally administering an effective amount of a Type IV phosphodiesterase inhibitor to an individual in need of such therapy.

It is another object of the invention to provide such a method wherein the Type IV phosphodiesterase inhibitor is administered transurethrally.

It is still another object of the invention to provide such a method wherein the phosphodiesterase inhibitor is administered via intracavernosal injection.

It is yet another object of the invention to provide such a method wherein the phosphodiesterase inhibitor is administered topically.

It is a further object of the invention to provide such a method wherein the phosphodiesterase inhibitor is administered transdermally.

It is yet a further object of the invention to provide pharmaceutical formulations for carrying out the aforementioned methods.

It is an additional object of the invention to provide a kit for administering a Type IV phosphodiesterase inhibitor as provided herein.

Additional objects, advantages and novel features of the invention will be set forth in part in the description that follows, and in part will become apparent to those skilled in the art upon examination of the following, or may be learned by practice of the invention.

In a first aspect of the invention, a method is provided for treating an individual prone to erectile dysfunction, e.g., vasculogenic erectile dysfunction, the method comprising locally administering to the individual a pharmaceutical formulation containing a Type IV phosphodiesterase inhibitor. Administration of the pharmaceutical formulation is carried out within the context of a predetermined dosing regimen such that the agent is effective in the treatment of erectile dysfunction. The method is especially useful in the treatment of vasculogenic impotence, although other types of erectile dysfunction may also be treated using the present formulations. Drug delivery is preferably effected transurethrally, but the drug may also be administered via intracavernosal injection or using topical or transdermal administration.

In another aspect of the invention, a pharmaceutical formulation is provided for carrying out the present method for treating erectile dysfunction. The pharmaceutical formulation comprises an effective amount of a Type IV phosphodiesterase inhibitor, a carrier suitable for the selected mode of administration, and, optionally, a permeation enhancer. The formulation may contain one or more additional active agents, including, for example, dopaminergic drugs, smooth muscle relaxants, vasoactive drugs, and additional phosphodiesterase inhibitors, and/or additives such as excipients, surfactants, preservatives (e.g., antioxidants), stabilizers, chelating agents, enzyme inhibitors, antibacterial agents and the like, as will be appreciated by those skilled in the art of drug formulation preparation and delivery.

In a further aspect of the invention, a kit is provided to assist an individual in drug administration to carry out the method of the invention. Generally, the kit will include the following components: a pharmaceutical formulation comprising the phosphodiesterase inhibitor to be administered; a device for effecting delivery of the pharmaceutical formulation; a container housing the pharmaceutical formulation during storage and prior to use; and instructions for carrying out drug administration in a manner effective to treat erectile dysfunction.

DETAILED DESCRIPTION OF THE INVENTION

Figure 1:
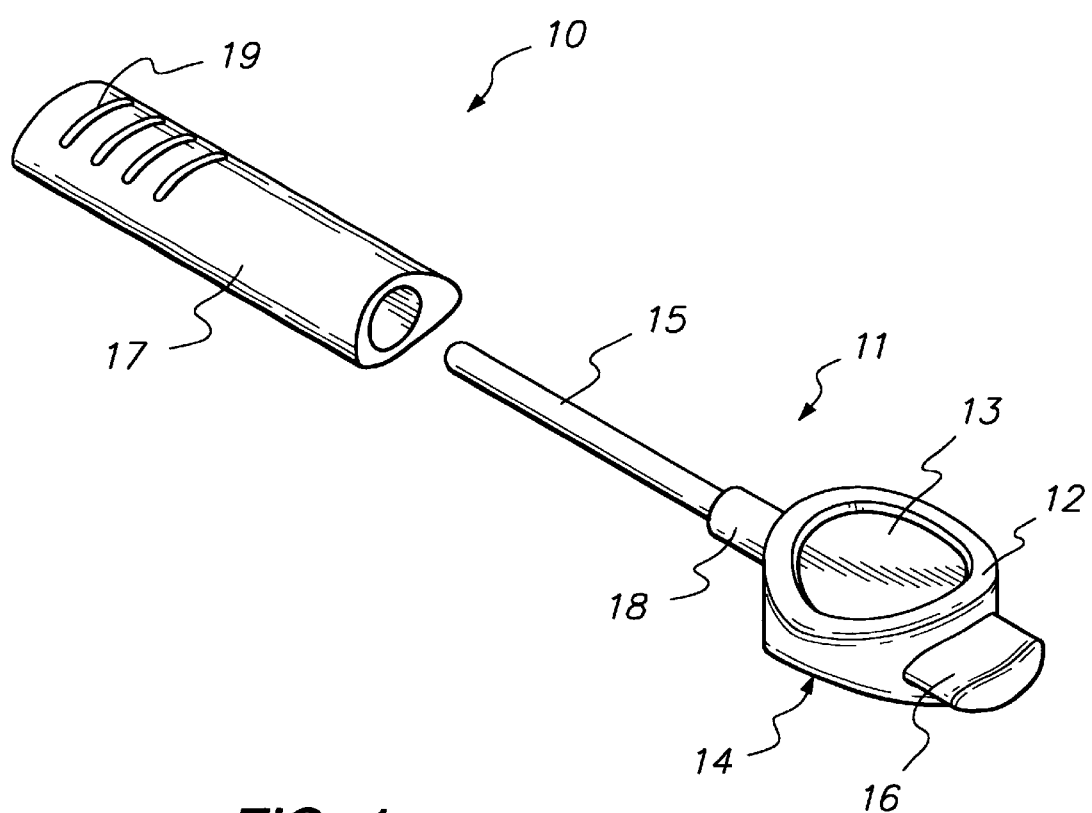
FIG. 1 is an exploded view of one embodiment of a transurethral drug administration device which may be used in conjunction with the present method.

DEFINITIONS:

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a Type IV phosphodiesterase inhibitor" includes a mixture of two or more Type IV phosphodiesterase inhibitors, reference to "a carrier" includes mixtures of two or more carriers, and the like.

In describing and claiming the present invention, the following terminology will be used in accordance with the definitions set out below.

The term "erectile dysfunction" is intended to include any and all types of erectile dysfunction, including: vasculogenic, neurogenic, endocrinologic and psychogenic impotence ("impotence" is used here in its broadest sense to indicate an inability a periodic or consistent inability to achieve or sustain an erection of sufficient rigidity for sexual intercourse; see U.S. Pat. No. 5,242,391 to Place et al., cited supra); Peyronie's syndrome; priapism; premature ejaculation; and any other condition, disease or disorder, regardless of cause or origin, which interferes with at least one of the three phases of human sexual response, i.e., desire, excitement and orgasm (see Kaplan, *Disorders of Sexual Desire* (New York, N.Y.: Brunner Mazel Book Inc., 1979)). Generally, however, the erectile dysfunction referred to herein is vasculogenic erectile dysfunction, particularly vasculogenic impotence.

The terms "treating" and "treatment" as used herein refer to reduction in severity and/or frequency of symptoms, elimination of symptoms and/or underlying cause, prevention of the occurrence of symptoms and/or their underlying cause, and improvement or remediaton of damage. The present method of "treating" erectile dysfunction, as the term is used herein, thus encompasses both prevention of the disorder in a predisposed individual and treatment of the disorder in a clinically symptomatic individual.

The term "phosphodiesterase inhibitor" as used herein is intended to mean an agent that is capable of inhibiting or selectively reducing the activity of any one or more phosphodiesterases.

The terms "active agent," "drug" and "pharmacologically active agent" are used interchangeably herein to refer to a chemical material or compound that induces a desired effect. In the preferred embodiment herein, the terms refer to a phosphodiesterase inhibitor which is capable of being delivered locally, preferably transurethrally typically, or by intracavernosal injection. Included are derivatives and analogs of those compounds or classes of compounds specifically mentioned which also induce the desired effect.

The terms "transurethral," "intraurethral" and "urethral" are used interchangeably to refer to the delivery of the drug into the urethra such that drug contacts and passes through the wall of the urethra.

The term "intracavernosal" as used herein refers to a mode of drug administration that involves injection into one or both corpora of the corpora cavernosal tissues.

The term "transdermal" delivery includes both transdermal (or "percutaneous") and transmucosal administration, i.e., delivery by passage of a drug through the body surface, i.e., the skin or mucosal tissue. "Transdermal" delivery is also intended to encompass delivery of a drug by passage across scrotal tissue.

The term "topical administration" is used in its conventional sense to mean delivery of a topical drug or pharmacologically active agent to the skin or mucosa.

"Penetration enhancement" or "permeation enhancement" as used herein relates to an increase in the permeability of the urethral wall to the selected pharmacologically active agent, i.e., so that the rate at which the drug permeates through the urethral wall is increased.

"Carriers" or "vehicles" as used herein refer to carrier materials suitable for local drug administration. Carriers and vehicles useful herein include any such materials known in the art which is nontoxic and does not interact with other components of the composition in a deleterious manner.

By an "effective" amount of a drug or pharmacologically active agent is meant a nontoxic but sufficient amount of the drug or agent to provide the desired effect, i.e., treatment of erectile dysfunction.

ACTIVE AGENTS FOR TREATMENT OF ERECTILE DYSFUNCTION:

In order to carry out the method of the invention, a selected Type IV phosphodiesterase inhibitor is locally administered to an individual prone to erectile dysfunction.

Examples of Type IV phosphodiesterase inhibitors that may be administered herein include, but are not limited to: pyrrolidinones such as rolipram (4-(3-cyclopentyloxy-4'-methoxyphenyl)-2-pyrrolidinone)) and rolipram derivatives such as RO20-1724 (4-(3-butyloxy-4-methoxyphenyl)-imidazolidinone) and RS 33793 (8-(3-nitrophenyl)-6-(3-methyl-2-butenyl)pyrido[2,3a]pyrazin-5-one); quinazolinediones such as nitraquazone (3-[3'-nitrophenyl] N-ethylquinazoline-2,6-dione), CP-77059 (1-(carbomethoxyphenyl)-3-benzylpyrido[2,3d] pyrimidine-2, 4(1H,3H)dione), RS-25344 (1-(3-nitrophenyl)-3-(4-pyridylmethyl)-1,2,3,4-tetrahydro pyrido(2,3-d) pyrimidine-2,4-dione)) and other nitraquazone analogs; xanthine derivatives such as denbufylline (1,3-di-n-butyl-7-[2'-oxopropyl] xanthine), XT-44 (1-n-butyl-3-n-propylxanthine), arofylline (LAS 31025; 1-propyl-3-(4-chlorophenyl)-xanthine) and BRL 61063

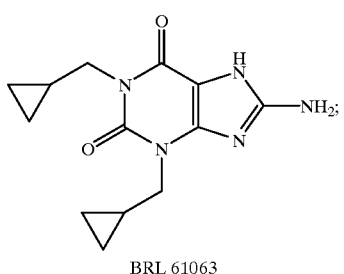

BRL 61063 phenyl ethyl pyridines such as CDP 840 (4-(1-(3-cyclopentyloxy-4-methoxyphenyl)-2-phenylethyl) pyridine) and compounds disclosed in WO 97/22585 to Guay et al.; tetrahydropyrimidones such as atizoram (CP 80633)

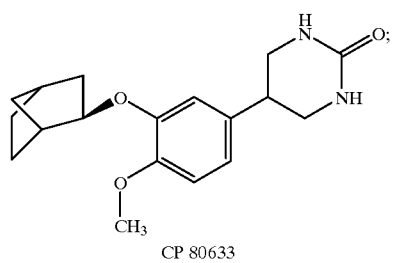

CP 80633 diazepine derivatives such as CI 1018

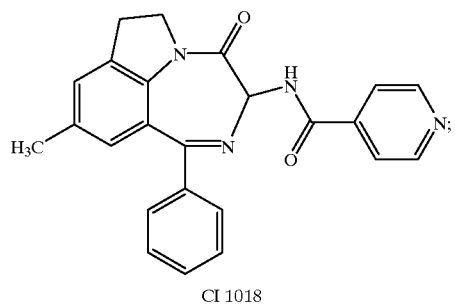

CI 1018 and compounds disclosed in WO 97/36905 to Pascal et al.; oxime carbamates such as filaminast (PDA-641); naphthyridinones such as RS 17597

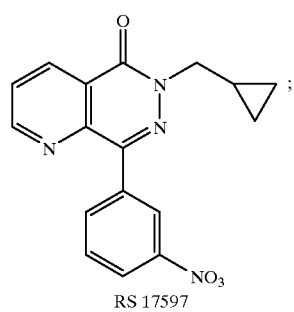

RS 17597 benzofurans such as 2-butyl-7-methoxy-benzofuran-4-carboxylic acid (3,5-dichloropyridin-4yl)-amide, 2-benzyl-7-methoxy-benzofuran-4-carboxylic acid (3,5-dichloropyridin-4-yl)-amide, 7-methoxy-2-phenethyl-benzofuran-4-carboxylic acid (3,5-dichloropyridin-4-yl)-amide and 5-(2-butyl-7-methoxy-benzofuran-4-yl)-tetrahydro-pyrimidin-2-one, phenyldihydrobenzofurane compounds such as those disclosed in U.S. Pat. No. 5,902,824; 4-substituted benzofurane compounds such as those disclosed in EP 819688A1; substituted furans as disclosed in Perrier et al. *Bioorg. Med. Chem. Lett.* 9:323–326 (1999); naphthalene derivatives such as T 440

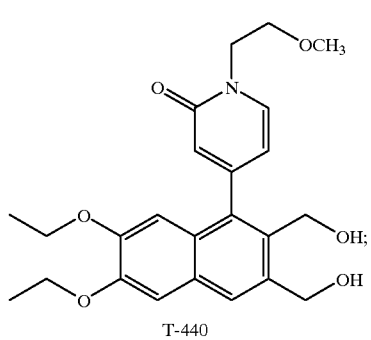

T-440 purine derivatives such as V 112294A

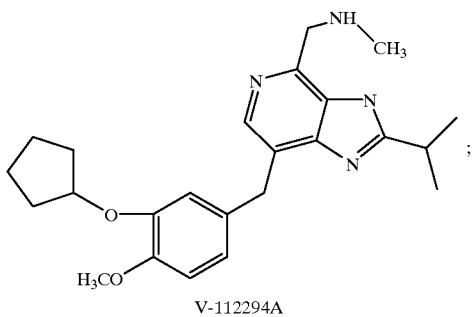

V-112294A cyclohexane carboxylic acids such as ariflo (SB 207499, (c-4-cyano-4-[3'-cyclopentyloxy-4'-methoxyphenyl]-r-1-cyclohexanecarboxylic acid)); benzamides such as piclamilast (RP73401; N-(3,5-dichloro-4-pyridyl)-3-cyclopentoxy-4-methoxy benzamide); benzothiophenes such as tibenelast (LY 186655); pyridopyridazinones such as

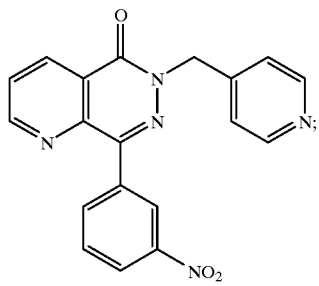

imidazolidinones such as

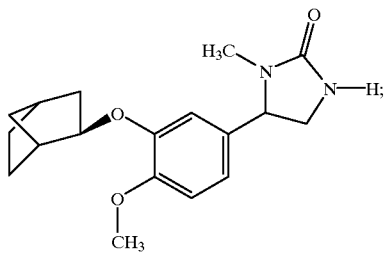

substituted phenyl compounds, as disclosed in U.S. Pat. No. 5,891,896 to Warrellow et al.; substituted biphenyl compounds as disclosed in U.S. Pat. No. 5,877,190 to Dhainaut et al.; etazolate; and S-(+)-glaucine ((S)-(+)-1,2,9,10-tetramethoxyaporphine).

Additional pharmacologically active agents may be delivered along with the primary active agent, i.e., the phosphodiesterase inhibitor. Vasoactive agents, particularly vasodilators, are preferred additional agents. Suitable vasoactive agents include, but are not limited to, nitrovasodilators such as: nitroglycerin; linsidomine, particularly linsidomine chlorhydrate ("SIN-1"); molsidomine; organic nitrates such as isosorbide dinitrate, erythrityl tetranitrate and amyl nitrate; sodium nitroprusside; S-nitrosothiols such as S-nitroso-N-acetyl-d,l-penicillamine ("SNAP"), S-nitroso-N-cysteine and S-nitroso-N-glutathione ("SNO-GLU"); and diazenium diolates ("NONOates") such as (Z)-1-{N-methyl-N-[6-(N-methyl-ammoniohexyl)amino]}diazen-1-ium-1,2-diolate, (Z)-1-[N-(3-ammoniopropyl)-N-(n-propyl)amino]diazen-1-ium-1,2-diolate, (Z)-1-{N-[3-aminopropyl]-N-[4-(3-aminopropylammonio)butyl]amino}diazen-1-ium-1,2-diolate and sodium (Z)-1-(N,N-diethylamino)-diazen-1-ium-1,2-diolate. Other suitable vasoactive agents include, for example, long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodipine, pinacidil, cyclandelate and isoxsuprine; chlorpromazine; haloperidol; yohimbine; Rec15/2739; trazodone; naturally occurring prostaglandins such as $PGE_0$, $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$; semisynthetic or synthetic derivatives of natural prostaglandins, including carboprost tromethamine, dinoprost tromethamine, dinoprostone, lipoprost, gemeprost, metenoprost, sulprostone and tiaprost; and vasoactive intestinal peptide. Prazosin, prostaglandin $E_0$, prostaglandin $E_1$ and prostaglandin $E_2$ are particularly preferred vasoactive agents to be co-administered with the active agent. The Type IV PDE inhibitors herein may also be administered in combination with one or more other types of PDE inhibitors, particularly, although not necessarily, a Type III PDE inhibitor, a Type V PDE inhibitor, and/or a nonspecific PDE inhibitor.

Suitable Type III inhibitors include, but are not limited to, bipyridines such as milrinone and amrinone; imidazolones such as piroximone and enoximone; imidazolines such as imazodan and 5-methyl-imazodan; dihydropyridazinones such as indolidan and LY181512

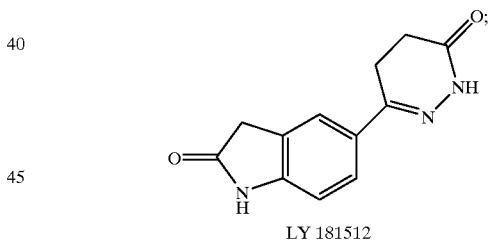

LY 181512 dihydroquinolinone compounds such as cilostamide, cilostazol, vesnarinone and OPC 3911

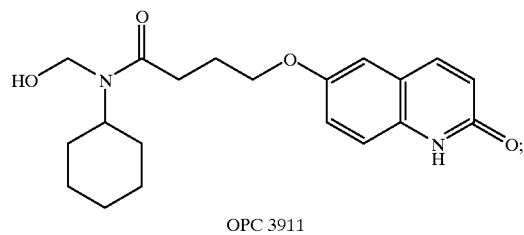

OPC 3911 other compounds such as anagrelide, bemoradan, ibudilast, isomazole, lixazinone, motapizone, olprinone, phthalazinol, pimobendan, quazinone, siguazodan and trequinsin; and mixed Type III and Type IV inhibitors such as benafentrine, cis-6-[p-acetamidophenyl]-1,2,3,4,4a,10b-hexahydro-8,9- dimethoxy-2-methylbenzo-[c][1,6]-naphthyridine, EMD 54622 (5-[1-(3,4-dimethoxybenzoyl)-4,4-dimethyl-1,2,3,4-tetrahydrochinolin-6-yl]-6-methyl-3,6-dihydro-1,3,4-thiadiazin-2-one), Org 20241 (N-hydroxy-4-[3,4-dimethoxyphenyl]-thiazole-2-carboximidamide), Org30029 (N-hydroxy-5,6-dimethoxybenzo-[b]-thiophene-2-carboximidamide), saterinone, tolafentrine and zardaverine.

Examples of type V phosphodiesterase inhibitors include, but are not limited to, zaprinast, MY5445, dipyridamole and sildenafil. Other type V phosphodiesterase inhibitors are disclosed in PCT Publication Nos. WO 94/28902 and WO 96/16644.

The compounds described in PCT Publication No. WO 94/28902 are pyrazolopyrimidinones. Examples of the inhibitor compounds include 5-(2-ethoxy-5-morpholinoacetylphenyl)-1-methyl-3-n-propyl-1,6-dihydro-7H-pyrazolo[4,3-d]pyrimidin-7-one, 5-(5-morpholinoacetyl-2-n-propoxyphenyl)-1-methyl-3-n-propyl-1,6-dihydro-7H-pyrazolo[4,3-d]pyrimidin-7-one, 5-[2-ethoxy-5-(4-methyl-1-piperazinylsulfonyl)-phenyl]-1-methyl-3-n-propyl-1,6-dihydro-7H-pyrazolo[4,3-d]pyrimidin-7-one, 5-[2-allyloxy-5-(4-methyl-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-propyl)-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-hydroxyethyl)-1-piperazinylsulfonyl)phenyl]-1-methyl-3-n-propyl-1,6-dihydro-7H-pyrazolo[4,3-d]pyrimidin-7-one, 5-[5-[4-(2-hydroxyethyl)-1-piperazinylsulfonyl]-2-n-propoxyphenyl]-1-methyl-3-n-propyl-1,6-dihydro-7H-pyrazolo[4,3-d]pyrimidin-7-one, 5-[2-ethoxy-5-(4-methyl-1-piperazinylcarbonyl)phenyl]-1-methyl-3-n-propyl-1,6-dihydro-7H-pyrazolo[4,3-d]pyrimidin-7-one and 5-[2-ethoxy-5-(1-methyl-2-imidazolyl)phenyl]-1-methyl-3-n-propyl-1,6-dihydro-7H-pyrazolo[4,3-d]pyrimidin-7-one.

The phosphodiesterase inhibitors described in PCT Publication No. WO 96/16644 include griseolic acid derivatives, 2-phenylpurinone derivatives, phenylpyridone derivatives, fused and condensed pyrimidines, pyrimidopyrimidine derivatives, purine compounds, quinazoline compounds, phenylpyrimidinone derivative, imidazoquinoxalinone derivatives or aza analogues thereof, phenylpyridone derivatives, and others. Specific examples of the phosphodiesterase inhibitors disclosed in WO 96/16644 include 1,3-dimethyl-5-benzylpyrazolo[4,3-d]pyrimidine-7-one, 2-(2-propoxyphenyl)-6-purinone, 6-(2-propoxyphenyl)-1,2-dihydro-2-oxypyridine-3-carboxamide, 2-(2-propoxyphenyl)-pyrido[2,3-d]pyrimid-4(3H)-one, 7-methylthio-4-oxo-2-(2-propoxyphenyl)-3,4-dihydro-pyrimido[4,5-d]pyrimidine, 6-hydroxy-2-(2-propoxyphenyl)pyrimidine-4-carboxamide, 1-ethyl-3-methylimidazo[1,5a]quinoxalin-4(5H)-one, 4-phenylmethylamino-6-chloro-2-(1-imidazoloyl)quinazoline, 5-ethyl-8-[3-(N-cyclohexyl-N-methylcarbamoyl)-propyloxy]-4,5-dihydro-4-oxo-pyrido[3,2-e]-pyrrolo[1,2-a]pyrazine, 5'-methyl-3'-(phenylmethyl)-spiro[cyclopentane-1,7'(8'H)-(3'H)-imidazo[2,1-b]purin]4' (5'H)-one, 1-[6-chloro-4-(3,4-methylenedioxybenzyl)-aminoquinazolin-2-yl)piperidine-4-carboxylic acid, (6R, 9S)-2-(4-trifluoromethyl-phenyl)methyl-5-methyl-3,4,5,6a,7,8,9,9a-octahydrocyclopent[4,5]-imidazo[2,1-b]-purin-4-one, 1-t-butyl-3-phenylmethyl-6-(4-pyridyl)pyrazolo[3,4-d]-pyrimid-4-one, 1-cyclopentyl-3-methyl-6-(4-pyridyl)-4,5-dihydro-1H-pyrazolo[3,4-d]pyrimid-4-one, 2-butyl-1-(2-chlorobenzyl)6-ethoxy-carbonylbenzimidaole and 2-(4-carboxypiperidino)-4-(3,4-methylenedioxy-benzyl)amino-6-nitroquinazoline and 2-phenyl-8-ethoxycycloheptimidazole.

Still other type V phosphodiesterase inhibitors include: IC-351 (ICOS); 4-bromo-5-(pyridylmethylamino)-6-[3-(4-chlorophenyl)propoxy]-3(2H)pyridazinone; 1-[4- [(1,3-benzodioxol-5-ylmethyl)amiono]-6-chloro-2-quinazolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]imidazo[2,1-b]purin-4-one; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; 1-methyl-5-(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); and Sch-51866.

Other phosphodiesterase inhibitors that may be co-administered with the Type IV PDE inhibitor include nonspecific phosphodiesterase inhibitors such as theophylline, theobromine, IBMX, pentoxifylline and papaverine, and direct vasodilators such as hydralazine.

The active agents may be administered, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). For example, acid addition salts are prepared from the free base using conventional methodology, and involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of acid moieties which may be present on a phosphodiesterase inhibitor molecule are prepared in a similar manner using a pharmaceutically acceptable base such as sodium hydroxide, potassium hydroxide, ammonium hydroxide, calcium hydroxide, trimethylamine, or the like. Particularly preferred basic salts herein are alkali metal salts, e.g., the sodium salt, and copper salts. Preparation of esters involves functionalization of hydroxyl and/or carboxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety which results in a compound that is therapeutically inactive until modified by an individual's metabolic system.

PHARMACEUTICAL FORMULATIONS AND MODES OF ADMINISTRATION:

The active agent is administered locally to treat erectile dysfunction, and is accordingly administered in a pharmaceutical formulation suitable for local administration.

Depending on the specific, "local" mode of administration, the pharmaceutical compositions may be in the form of solid, semi-solid or liquid dosage forms, such as, for example, suppositories, powders, liquids, suspensions, creams, ointments, lotions or the like, preferably in unit dosage form suitable for single administration of a precise dosage. The compositions comprise an effective amount of the phosphodiesterase inhibitor in combination with a pharmaceutically acceptable carrier and, in addition, may include other pharmaceutical agents, adjuvants, diluents, buffers, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington: *The Science and Practice of Pharmacy, Nineteenth Ed.* (Easton, Pa.: Mack Publishing Company, 1995).

The formulation may, for example, be administered transurethrally. For transurethral administration, the formulation comprises a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

Depending on the particular phosphodiesterase inhibitor administered, it may be desirable to incorporate a transurethral permeation enhancer in the urethral dosage form. Examples of suitable transurethral permeation enhancers include dimethylsulfoxide ("DMSO"), dimethyl formamide ("DMF"), N,N-dimethylacetamide ("DMA"), decylmethylsulfoxide ("$C_{10}$MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), SEPA® (available from Macrochem Co., Lexington, Mass.), alcohols (e.g., ethanol), surfactants as discussed above, including, for example, Tergitol®, Nonoxynol-9® and TWEEN-80®, and lower alkanols such as ethanol.

Transurethral formulations may additionally include one or more enzyme inhibitors effective to inhibit drug-degrading enzymes which may be present in the urethra. Such enzyme inhibiting compounds may be determined by those skilled in the art by reference to the pertinent literature and/or using routine experimental methods. Additional optional components include excipients, preservatives (e.g., antioxidants), chelating agents, solubilizing agents (e.g., surfactants), and the like, as will be appreciated by those skilled in the art of drug formulation preparation and delivery.

Transurethral drug administration, as explained in U.S. Pat. Nos. 5,242,391, 5,474,535, 5,686,093 and 5,773,020 to Place et al., can be carried out in a number of different ways using a variety of urethral dosage forms. For example, the drug can be introduced into the urethra from a flexible tube, squeeze bottle, pump or aerosol spray. The drug may also be contained in coatings, pellets or suppositories which are absorbed, melted or bioeroded in the urethra. In certain embodiments, the drug is included in a coating on the exterior surface of a penile insert. A preferred drug delivery device for administering a drug transurethrally is shown in FIG. 1. It is preferred, although not essential, that the drug be delivered at least about 3 cm into the urethra. Generally, delivery at about 3 cm to about 8 cm into the urethra will provide effective results in conjunction with the present method.

Urethral suppository formulations containing PEG or a PEG derivative are particularly preferred urethral dosage forms herein, and may be conveniently formulated using conventional techniques, e.g., compression molding, heat molding or the like, as will be appreciated by those skilled in the art and as described in the pertinent literature and pharmaceutical texts. See, for example, Remington: *The Science and Practice of Pharmacy, Nineteenth Ed.*, cited previously, which discloses typical methods of preparing pharmaceutical compositions in the form of urethral suppositories. The PEG or PEG derivative preferably has a molecular weight $M_w$ in the range of about 200 to 2500, more preferably in the range of about 1000 to 2000. Suitable polyethylene glycol derivatives include polyethylene glycol fatty acid esters, for example, polyethylene glycol monostearate, polyethylene glycol sorbitan esters, e.g., polysorbates, and the like. It is also preferred that urethral suppositories contain one or more solubilizing agents effective to increase the solubility of the active agent in the PEG or other transurethral vehicle.

The solubilizing agent may be a nonionic, anionic, cationic or amphoteric surfactant. Nonionic surfactants include: long-chain fatty acids, i.e., acids having the structural formula $CH_3(CH_2)_m COOH$ where m is an integer in the range of 8 to 16; fatty alcohols, that is, alcohols having the structural formula $CH_3(CH_2)_m C(H)OH$, such as lauryl, cetyl and stearyl alcohols; glyceryl esters such as the naturally occurring mono-, di- and triglycerides; and esters of fatty alcohols or other alcohols such as propylene glycol, polyethylene glycol, sorbitan, sucrose and cholesterol. Examples of water-soluble nonionic surfactant derivatives include sorbitan fatty acid esters (such as those sold under the trade name Span®), polyoxyethylene sorbitan fatty acid esters (such as those sold under the trade name TWEEN®), polyoxyethylene fatty acid esters (such as those sold under the trade name Myrj®), polyoxyethylene steroidal esters, polyoxypropylene sorbitan fatty acid esters, polyoxypropylene fatty acid esters, polyoxypropylene steroidal esters, polyoxyethylene ethers (such as those sold under the trade name Brij®), polyglycol ethers (such as those sold under the trade name Tergitol®), and the like. Preferred nonionic surfactants for use as the solubilizing agent herein are polyglycol ether, polyoxyethylene sorbitan trioleate, sorbitan monopalmitate, polysorbate 80, polyoxyethylene 4-lauryl ether, propylene glycol, and mixtures thereof. Anionic surfactants which may be used as the solubilizing agent herein include long-chain alkyl sulfonates, carboxylates and sulfates, as well as alkyl aryl sulfonates, and the like. Preferred anionic surfactants are sodium dodecyl sulfate, dialkyl sodium sulfosuccinate (e.g., sodium bis-(2-ethylhexyl)-sulfosuccinate), sodium 7-ethyl-2-methyl-4-dodecyl sulfate and sodium dodecylbenzene sulfonate. Cationic surfactants which may be used to solubilize the active agent are generally long-chain amine salts or quaternary ammonium salts, e.g., decyltrimethyl-ammonium bromide, dodecyltrimethylammonium bromide, tetradecyltrimethylammonium bromide, tetradecyltrimethylammonium chloride, and the like. Amphoteric surfactants are generally, although not necessarily, compounds which include a carboxylate or phosphate group as the anion and an amino or quaternary ammonium moiety as the cation. These include, for example, various polypeptides, proteins, alkyl betaines, and natural phospholipids such as lecithins and cephalins. Other suitable solubilizing agents (e.g., glycerin) may also be used, as will be appreciated by those skilled in the art. The solubilizing agent will be present in the range of approximately 0.01 wt. % to 40 wt. %, more preferably in the range of approximately 5.0 wt. % to 40 wt. %, and most preferably in the range of approximately 10.0 wt. % to 40 wt. %.

It may be desirable to deliver the active agent in a urethral dosage form which provides for controlled or sustained release of the agent. In such a case, the dosage form typically comprises a biocompatible, biodegradable material, typically a biodegradable polymer. Examples of such polymers include polyester, polyalkylcyanoacrylate, polyorthoester, polyanhydride, albumin, gelatin and starch. As explained, for example, in PCT Publication No. WO96/40054, these and other polymers can be used to provide biodegradable microparticles which enable controlled and sustained drug release, in turn minimizing the required dosing frequency.

The urethral dosage form will preferably comprise a suppository that is on the order of 2 to 20 mm, preferably 5 to 10 mm, in length and less than about 5 mm, preferably less than about 2 mm in width. The weight of the suppository will typically be in the range of approximately 1 mg to 100 mg, preferably in the range of approximately 1 mg to 50 mg. However, it will be appreciated by those skilled in the art that the size of the suppository can and will vary, depending on the potency of the drug, the nature of the formulation, and other factors.

In FIG. 1, a suitable transurethral drug delivery device is shown generally at 10. The device comprises a transurethral inserter 11 having an easily graspable segment 12 that has opposing symmetrically concave surfaces 13 and 14 adapted to be held by two fingers. Drug is contained within a urethral suppository (not shown) within shaft 15, which is sized to fit within the urethra. A longitudinal plunger, the tip of which is seen at 16, is slidably insertable into the longitudinal bore contained within shaft 15. To extrude drug into the urethra, shaft 15 is inserted into the urethra, and plunger tip 16 is pushed into segment 12. The inserter 11 is then removed. Prior to use, and during storage, the device is capped with elongate cap 17 which fits snugly over flange 18 at the proximal end of shaft 15. The cap 17 is provided with a series of parallel ridges 19 to facilitate gripping of the cap and removal from inserter 11.

Although the transurethral drug delivery device shown in FIG. 1 represents a preferred device for use herein, again, it should be emphasized that a wide variety of device configurations and urethral dosage forms can be used. Examples of other devices suited to deliver a drug transurethrally are those described and illustrated in PCT Publication No. WO 91/16021 and in U.S. Pat. Nos. 5,242,391, 5,474,535, 5,686, 093 and 5,773,020 to Place et al.

The devices can either be manufactured under sterile conditions, thereby eliminating the need for post-manufacturing sterilization, or they can be manufactured under non-sterile conditions and then subsequently sterilized by any suitable technique, e.g., radiation sterilization. The devices can be manufactured by typical plastic forming and coating processes known in the art, including molding extrusion, heat forming, dip coating, and the like.

Transurethral drug delivery may involve an "active" delivery mechanism such as iontophoresis, electroporation or phonophoresis. Devices and methods for delivering drugs in this way are well known in the art. Iontophoretically assisted drug delivery is, for example, described in PCT Publication No. WO96/40054, cited above. Briefly, the active agent is driven through the urethral wall by means of an electric current passed from an external electrode to a second electrode contained within or affixed to a urethral probe.

Other modes of "local" drug administration can also be employed. For example, the selected active agent may be administered by way of intracavernosal injection, or it may be administered topically, in an ointment, gel or the like, or transdermally, including transscrotally, using a conventional transdermal drug delivery system.

Intracavernosal injection can be carried out by use of a syringe any other suitable device. An example of a hypodermic syringe useful herein, that can be used for simultaneous injection into both corpora, is described in U.S. Pat. No. 4,127,118 to Latorre. The injection is made on the dorsum of the penis by placement of the needle to the side of each dorsal vein and inserting it deep into the corpora.

For intracavernosal injection, the active agent to be administered is incorporated into a sterile liquid preparation, typically a solution or suspension in an aqueous or oleaginous medium. This solution or suspension may be formulated according to techniques known in the art using suitable carriers, dispersants, wetting agents, diluents, suspending agents or the like. Among the acceptable vehicles and solvents that may be employed are water, isotonic saline, vegetable oil, fatty esters and polyols.

The phosphodiesterase inhibitors useful herein may also be delivered through the skin using conventional transdermal drug delivery systems, i.e., transdermal "patches" wherein the agent is typically contained within a laminated structure that serves as a drug delivery device to be affixed to the skin. In such a structure, the drug composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery.

Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

Preferred formulations for topical drug delivery herein are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

The amount of active agent administered and the dosing regimen used, will, of course, be dependent on the particular drug selected, the age and general condition of the subject being treated, the severity of the subject's condition, and the judgment of the prescribing physician. Generally, the daily dosage when administered locally will be less than the dosage normally given in conjunction with systemic modes of administration, and typically, the drug will be administered one to four times daily or, with some active agents, just prior to intercourse. Alternatively, a large initial loading dose can be used to achieve effective levels of the agent and can be followed by smaller doses to maintain those levels. A typical daily dose of an active agent as administered locally is generally in the range of approximately 0.01 to 500 mg. Depending on the half-life of the drug and the availability via the chosen route of administration, the dosing regimen can be modulated in order to achieve satisfactory control of the onset of ejaculation. By administering the drug locally, the side effects, drug interactions and disease considerations of systemic (e.g., oral) drug administration are avoided, as is the stigma associated with psychotherapeutic drug therapy.

KITS:

The invention also encompasses a kit for patients to carry out the present method of treating erectile dysfunction using local drug therapy. The kit contains the pharmaceutical formulation to be administered, a device for administering the formulation (e.g., a transurethral drug delivery device such as shown in FIG. 1), a container, preferably sealed, for housing the drug and device during storage and prior to use, and instructions for carrying out drug administration in an effective manner. The formulation may consist of the drug in unit dosage form. The kit may contain multiple formulations of different dosages of the same agent. The kit may also contain multiple formulations of different active agents. The instructions may be in written or pictograph form, or can be on recorded media including audio tape, video tape, or the like.

USE IN CONJUNCTION WITH VENOUS FLOW CONTROL ("VFC") DEVICE:

In an alternative embodiment of the invention, a pharmaceutical formulation containing the selected phosphodiesterase inhibitor is administered in combination with use of a venous flow control device such as that described in U.S. Pat. No. 5,855,548 to Place for "Venous Flow Control Element for Maintaining Penile Erection," assigned to VIVUS, Inc. (Mountain View, Calif.). Preferred devices are formed from a length of flexible tubing having an integral fastening means, so as to provide for readily adjustable venous flow control when applied to the penis. The device is applied to the base of the penis prior to and during sexual intercourse, such that it effectively enhances retention of blood within the penis without substantially obstructing arterial inflow or becoming too constrictive during the erectile process. Use of the VFC device also enables enhanced effectiveness of local drug therapy, in that the active agent is retained within the penis, allowing movement into the corpus cavernosa. This produces smooth muscle response and a consistent erectile response. In this embodiment, a kit will include the venous flow control device in addition to the components noted above, along with instructions for using the device.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXAMPLE 1

Preparation of urethral dosage form: A transurethral pharmaceutical formulation containing rolipram, a Type IV phosphodiesterase inhibitor, is prepared by mixing 0.2 to 1.5 g of rolipram with a suitable amount of polyethylene glycol, typically 1–5 g, molecular weight ($M_w$) approximately 2000, and heating the mixture to a temperature just high enough to produce a drug-polymer melt. The mixture can then be poured into a mold suitable to provide a suppository, and allowed to cool. The suppository so provided is a unit dosage form suitable for transurethral administration. This procedure can be used with various Type IV phosphodiesterase inhibitors, PEGs, and additional components, e.g., enhancers or the like.

The aforementioned method may also be used to prepare urethral suppositories containing other phosphodiesterase inhibitors as the active agent.

EXAMPLE 2

A penile insert coated with rolipram is prepared as follows. An ethylene vinyl acetate rod is formed into an insert having a shaft approximately 10 cm long with a spherical, blunted tip. A dipping bath comprising a 50—50 weight blend of PEG 1450 and PEG 4000 and sufficient rolipram to attain the desired concentration in the coating is prepared and heated to 70° C. The insert is suspended by its head, dipped into the dipping bath and removed. A penile insert suitable for transurethral administration is thus provided.

The aforementioned procedure may be used to prepare penile inserts coated with any number of other Type IV phosphodiesterase inhibitors as well.

EXAMPLE 3

An effective phosphodiesterase-inhibiting dose may be determined using the following procedures.

Transurethral administration: Patients with penile vascular insufficiency are given a single dose of 0.5 g of a Type IV phosphodiesterase inhibitor (e.g., rolipram) transurethrally in a PEG-based urethral suppository. Prior to and approximately 3 hours after administering the inhibitor, blood samples are taken and assayed for plasma Type IV phosphodiesterase activity using, for example, high-performance liquid chromatography with fluorimetric detection as described by Lee et al, *J. Chromatography* 421:237–244 (1987). This procedure is repeated at 24 hour intervals with dosage adjusted as necessary.

EXAMPLE 4

The pharmaceutical preparations of Examples 1 and 2 can be used to treat erectile dysfunction in individuals in which the dysfunction is associated, for example, vascular insufficiency. Dosage may be adjusted using the methodology of Example 3. In all instances the individuals are expected to respond positively, although variations in the intensity and duration of erection may be observed depending on dose, formulation and environment. Generally, between approximately 20 and 90 minutes following drug administration, it is expected that an erection may be achieved.

EXAMPLE 5

In this experiment, rolipram was evaluated for its capability to induce erections in the anesthetized male cat. Adult male cats (3.5 to 5.0 kg) were initially sedated with ketamine and then anesthetized and maintained with supplemental doses of pentobarbital administered through a polyethylene catheter inserted into the left external jugular vein. After exposure of the pubic area, a 25-gauge needle was placed into the left corpus cavernosum for measurement of intracavernous pressure. Rolipram (Sigma Chemical, St. Louis, Mo.) was dissolved in 20% dimethylsulfoxide (DMSO) and diluted with 0.9% NaCl. Prostaglandin $E_1$ ($PGE_1$) (Sigma Chemical, St. Louis, Mo.) was dissolved in ethanol and diluted with 0.9% NaCl. Vehicle and various doses of rolipram (3, 10, 30 and 100 μg) were administered by direct injection into the right corpus cavernosum using a 30-gauge needle. All injections were made using a total volume of 200 μl. At the end of the experiment, each animal received a control drug solution containing 1.65 mg papaverine, 25 μg phentolamine and 0.5 μg of prostaglandin $E_1$ to establish maximal response in each subject.

Figure 2:
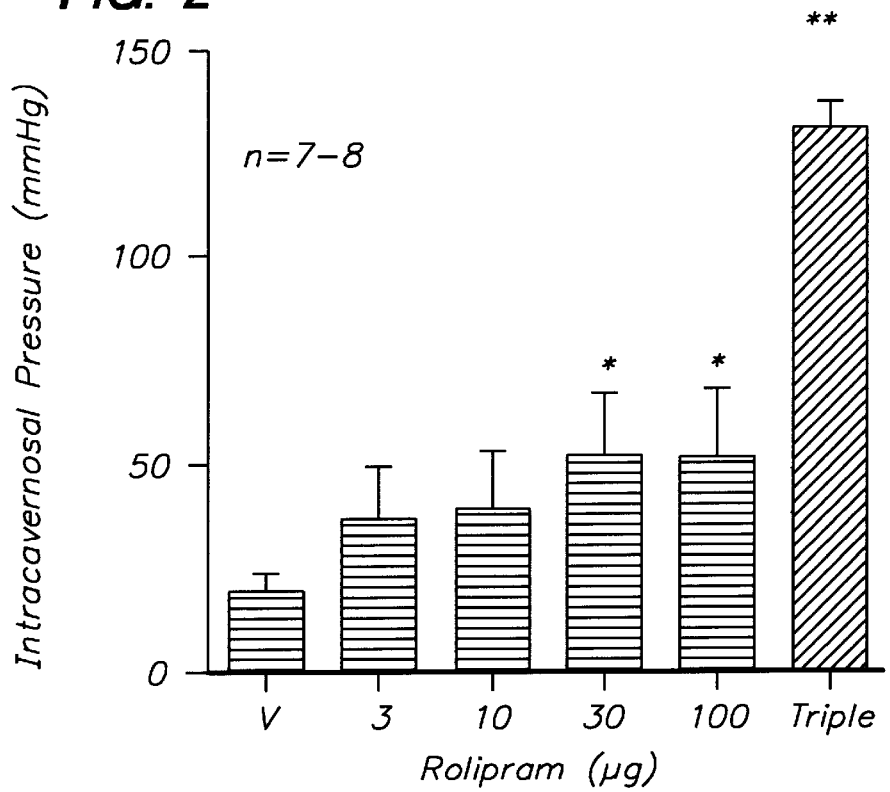
FIG. 2 is a bar graph illustrating the effect of intracavernosally administered rolipram, a Type IV PDE inhibitor, on intracavernosal pressure.
Figure 3:
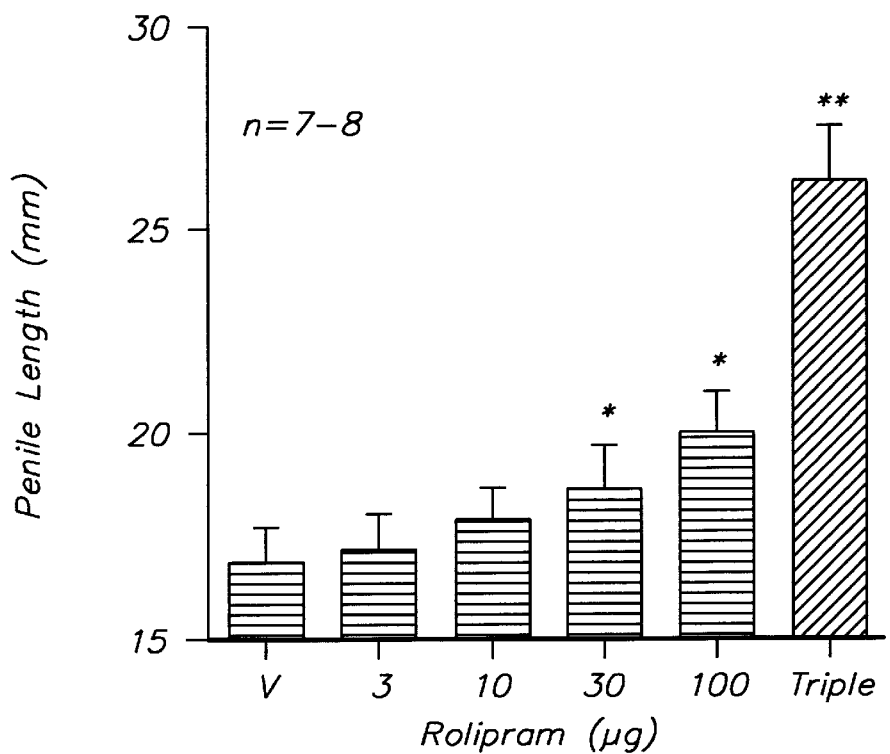
FIG. 3 is a bar graph illustrating the effect of intracavernosally administered rolipram on penile length, as evaluated in Example 5.

Intracavernosal injections of rolipram caused dose dependent increases in cavernosal pressure and penile length. These results are illustrated in FIG. 2 and FIG. 3, bar graphs showing intracavernosal pressure (FIG. 2) and penile length (FIG. 3) in response to intracavernosal injections of rolipram (3 to 100 μg). The maximal increase in cavernosal pressure in response to rolipram was an approximate three-fold increase from a baseline value of 20±2 mmHg. The 100 μg dose of rolipram produced 45±10% of the erectile response elicited by the standard control combination.

The duration of erectile responses and effects on systemic arterial pressure (ΔSAP) are summarized in Table 1. The erectile response resulting from the 100 μg dose of rolipram lasted 5±2 minutes. Intracavernosal injections of rolipram (3 and 10 μg) did not produce significant decreases in systemic arterial pressure, although higher doses did; the standard control combination caused a much larger decrease in systemic arterial pressure. In the figures and the table, "Triple" denotes response to the administration of the triple-drug control combination at the conclusion of a series of experiments. One asterisk indicates that the response to rolipram is significantly different from the response elicited by vehicle, with a p value of less than 0.05; two asterisks indicate that the p value was less than 0.01.

TABLE 1

Duration of Erectile Response and Change in Systemic Arterial Pressure (ΔSAP)

| Drug | Dose (μg) | Duration (minutes) | ΔSAP (mm Hg) |
| --- | --- | --- | --- |
| Rolipram | 3 | 2 ± 1 | 0 ± 0 |
| Rolipram | 10 | 2 ± 2 | −4 ± 2 |
| Rolipram | 30 | 3 ± 1 | −9 ± 2* |
| Rolipram | 100 | 5 ± 2 | −16 ± 5* |
| Triple | | 36 ± 9** | −42 ± 7** |

Figure 4:
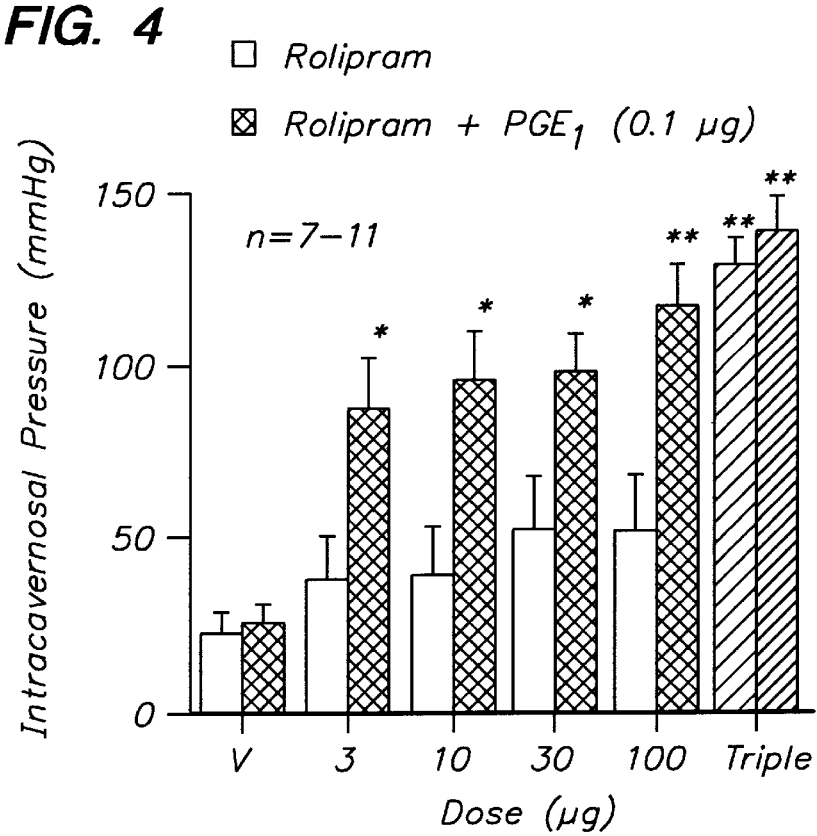
FIG. 4 is a bar graph illustrating the effect of intracavernosally administered rolipram, alone or in combination with prostaglandin $E_1$, on intracavernosal pressure (also as evaluated in Example 5).
Figure 5:
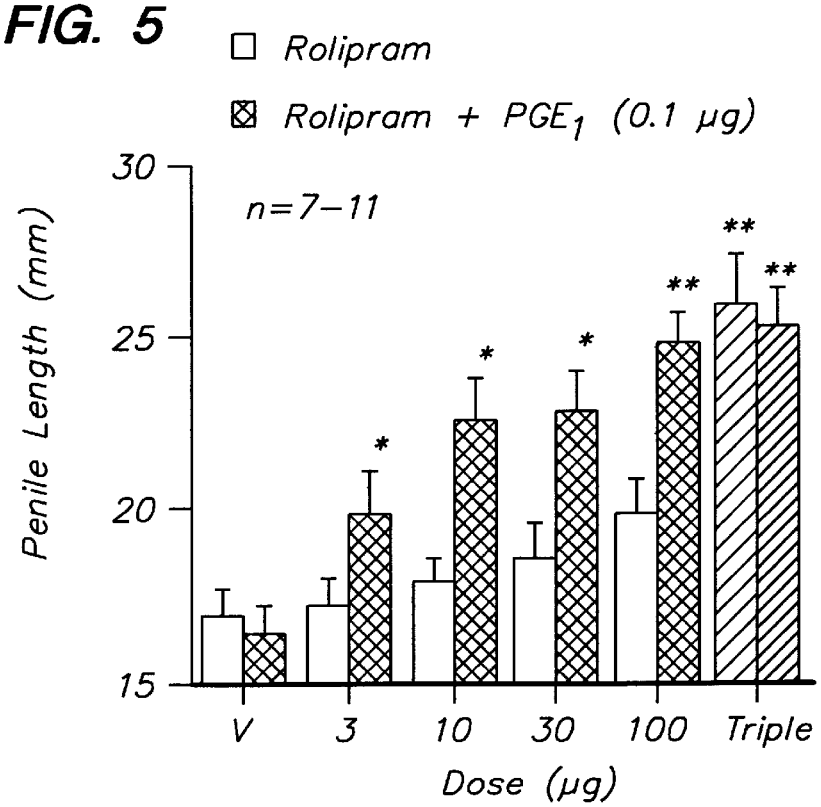
FIG. 5 is a bar graph illustrating the effect of intracavernosally administered rolipram, alone or in combination with prostaglandin $E_1$, on penile length (also as evaluated in Example 5).

In addition, intracavernosal injection of rolipram together with the prostaglandin $PGE_1$ (0.1 μg) significantly increased cavernosal pressure and penile length over the responses to rolipram alone. FIGS. 4 and 5 present bar graphs showing intracavernosal pressure (FIG. 4) and penile length (FIG. 5) in response to intracavernosal injections of rolipram (3 to 100 μg) alone and of rolipram combined with $PGE_1$ (0.1 μg). As illustrated in FIGS. 4 and 5, when rolipram was combined with $PGE_1$ and administered intracavernosally, all doses significantly (p<0.05) increased intracavernosal pressure and penile length significantly above the responses exhibited when rolipram was administered alone. Intracavernosal injections of rolipram alone caused increases in cavernosal pressure and penile length which were not comparable to the standard control combination (light hatched bar), while all doses of rolipram combined with $PGE_1$ elicited an erectile response which was similar to the control combination (dark hatched bar). A dose of $PGE_1$ (0.1 μg) without rolipram caused an increase in cavernosal pressure to 38±7 mm from a baseline of 24±3 mm Hg (not shown in FIG. 4).

Figure 6:
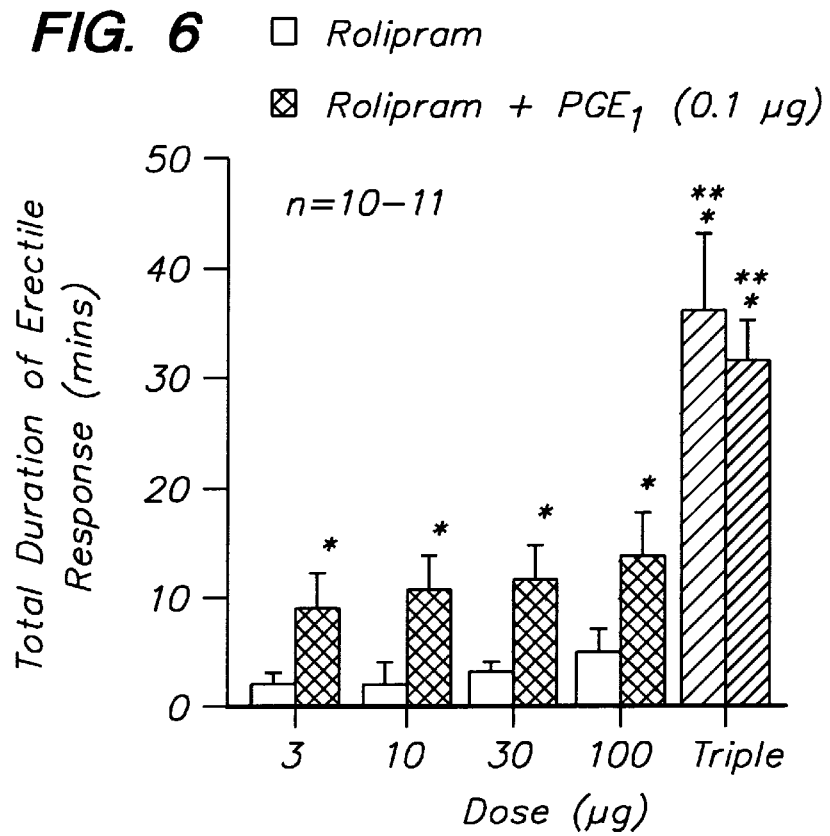
FIG. 6 is a bar graph illustrating the duration of erectile response to intracavernosal injections of rolipram, administered alone or in combination with prostaglandin $E_1$.

The duration of these rolipram+$PGE_1$ responses was also increased over the duration of the response to doses of rolipram alone. These results are illustrated in FIG. 6, which is a bar graph comparing the total duration of the erectile response to rolipram (3 to 100 μg) administered alone and in combination with $PGE_1$ (0.1 μg).

In these figures, "Triple" denotes response to the administration of the triple-drug control combination at the conclusion of a series of experiments (rolipram alone, lightly hatched bars; rolipram plus $PGE_1$, darkly hatched bars). One asterisk indicates that the response is significantly different from the response elicited by rolipram alone with a p value of less than 0.05; two asterisks indicate that the p value was less than 0.01.

These results demonstrate that a selective Type IV phosphodiesterase inhibitor, when administered locally, can induce significant increases in erectile response in a mammalian male. These increases in erectile response include dose-dependent increases in cavernosal pressure, penile length, and duration of erectile response. The same or greater effects are expected upon administration of a urethral suppository. In addition, these results demonstrate that co-administration of a selective Type IV phosphodiesterase inhibitor together with prostaglandin PGE, produced an enhanced, synergistic effect. Administration of a selective Type IV phosphodiesterase inhibitor together with prostaglandin PGE, produced an erectile response that was comparable to the effect observed with the triple-drug combination. Administration of a selective Type IV phosphodiesterase inhibitor together with a prostaglandin is expected to be even more effective than administration of a selective Type IV phosphodiesterase inhibitor alone. The combination of a prostaglandin, such as $PGE_1$, with a selective Type IV phosphodiesterase inhibitor is expected to be most effective as a local therapy for erectile dysfunction.

EXAMPLE 6

In this experiment, rolipram was evaluated for its capability to increase cAMP and cGMP concentrations in cultured smooth muscle cells from human corpora cavernosa. Human cavernosal smooth muscle cells in primary culture were prepared as described in Feldman et al., J. Urol. 151:54, 1994. Corporal tissue explants (1 to 2 mm) were obtained from patients undergoing penile prosthesis implantation. The fragments were placed into culture flasks containing growth media (Dulbecco's MEM containing 20% fetal bovine serum) and kept undisturbed for four days. The medium was exchanged with fresh growth media, and this exchange was repeated every 4 days until the cultures became confluent. The cells were trypsinized for confluent culture (2 to 4 passages) and plated on 12-well culture plates. The cells were incubated with $PGE_1$ (3 μM), rolipram (10 μM) or a combination of both $PGE_1$, (3 μM) and rolipram (10 μM), for up to two hours. The reaction was halted with the addition of 0.1 N HCl. The media was extracted by cold absolute ethanol and cells were lysed for the determination of cAMP and cGMP levels. The levels of cAMP and cGMP were measured (pmol/$10^6$ cells) using a commercially available EIA kit (R&D Systems, Minneapolis, Minn.).

Figure 7:
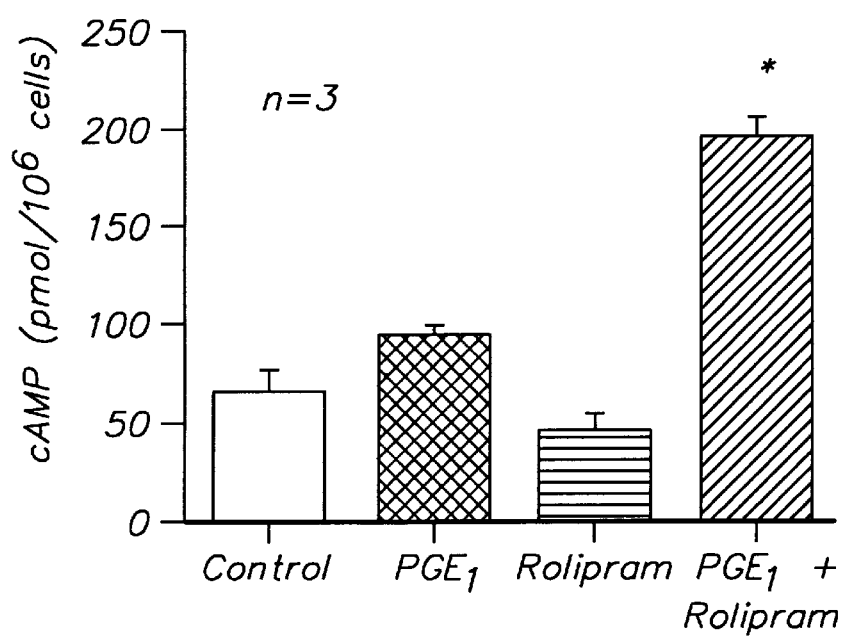
FIG. 7 is a bar graph showing intracellular cAMP levels in human cavernosal smooth muscle cells in primary culture following incubation with rolipram, prostaglandin $E_1$, and with the combination thereof, as evaluated in Example 6.

Cells in monolayer culture (80 to 90% confluence) at passages 2 to 3 were incubated with $PGE_1$ (3 μM), rolipram (10 μM) or the combination of $PGE_1$ (3 μM) and rolipram (10 μM) for up to 2 hours at 37° C. Cells incubated with $PGE_1$ (3 μM) responded with an approximate 22% increase in intracellular levels of cAMP (96±4 pmol./$10^6$ cells) compared with control values (66±11 pmol./$10^6$ cells). Rolipram in a dose of 10 μM did not increase intracellular levels of cAMP (49±8 pmol./$10^6$ cells) in human cavernosal smooth muscle cells. The combination of $PGE_1$ and rolipram significantly increased ($p<0.05$) intracellular levels of cAMP from 66±11 pmol./$10^6$ cells to 199±9 pmol./$10^6$ cells. These results are shown in FIG. 7, which is a bar graph showing levels of cAMP in human cavernosal smooth muscle cells in primary culture after incubation with $PGE_1$ (3 μM), rolipram (10 μM) and $PGE_1$ (3 μM) combined with rolipram (10 μM). The maximum increase in intracellular cAMP levels was exhibited after 15 minutes post-incubation with $PGE_1$ and rolipram and returned to baseline values after 2 hours. Intracellular levels of cGMP did not significantly increase in the presence of $PGE_1$, rolipram or the combination of $PGE_1$ and rolipram in human cavernosal smooth muscle cells. These results suggest a synergistic effect of rolipram with $PGE_1$. Similar effects are expected with other Type IV, cAMP-specific phosphodiesterase inhibitors, alone or in combination with prostaglandins such as $PGE_1$. The ability of Type IV, cAMP-specific phosphodiesterase inhibitors to influence penile erection, especially when combined with prostaglandins such as $PGE_1$, provides clinicians with novel therapeutic formulations for the treatment of erectile dysfunction.

What is claimed is:

1. A method for treating erectile dysfunction in a male individual, comprising locally administering to the individual a therapeutically effective amount of a pharmaceutical formulation comprised of a Type IV phosphodiesterase inhibitor or a pharmaceutically acceptable salt, ester, amide or prodrug thereof.

2. The method of claim 1, wherein the formulation further comprises a pharmaceutically acceptable carrier.

3. The method of claim 1, wherein the Type IV phosphodiesterase inhibitor is selected from the group consisting of pyrrolidinones, quinazolinediones, xanthine derivatives, phenyl ethyl pyridines, tetrahydropyrimidones, diazepine derivatives, oxime carbamates, naphthyridinones, benzofurans, naphthalene derivatives, purine derivatives, imidazolidinones, cyclohexane carboxylic acids, benzamides, pyridopyridazinones, benzothiophenes, etazolate, S-(+)-glaucine, substituted phenyl compounds and substituted biphenyl compounds.

4. The method of claim 3, wherein the Type IV phosphodiesterase inhibitor is a pyrrolidinone.

5. The method of claim 4, wherein the pyrrolidinone is selected from the group consisting of rolipram, RO20-1724 and RS 33793.

6. The method of claim 5, wherein the pyrrolidinone is rolipram.

7. The method of claim 3, wherein the Type IV phosphodiesterase inhibitor is a quinazolinedione.

8. The method of claim 5, wherein the quinazolinedione is selected from the group consisting of nitraquazone, CP-77059 and RS-25344.

9. The method of claim 3, wherein the Type IV phosphodiesterase inhibitor is a xanthine derivative.

10. The method of claim 9, wherein the xanthine derivative is selected from the group consisting of denbufylline, arofylline and BRL 61063.

11. The method of claim 3, wherein the Type IV phosphodiesterase inhibitor is a phenyl ethyl pyridine.

12. The method of claim 11, wherein the phenyl ethyl pyridine is CDP 840.

13. The method of claim 3, wherein the Type IV phosphodiesterase inhibitor is a tetrahydropyrimidone.

14. The method of claim 13, wherein the tetrahydropyrimidone is atizoram.

15. The method of claim 3, wherein the Type IV phosphodiesterase inhibitor is a diazepine derivative.

16. The method of claim 15, wherein the diazepine derivative is CI 1018.

17. The method of claim 3, wherein the Type IV phosphodiesterase inhibitor is an oxime carbamate.

18. The method of claim 17, wherein the oxime carbamate is filaminast.

19. The method of claim 3, wherein the Type IV phosphodiesterase inhibitor is a naphthyridinone.

20. The method of claim 19, wherein the naphthyridinone is RS 17597.

21. The method of claim 3, wherein the Type IV phosphodiesterase inhibitor is a benzofuran.

22. The method of claim 21, wherein the benzofuran is selected from the group consisting of 2-butyl-7-methoxy-benzofuran-4-carboxylic acid (3-5-dichloropyridin-4-yl)-amide, 2-benzyl-7-methoxy-benzofuran-4-carboxylic acid (3-5-dichloropyridin-4-yl)-amide, 7-methoxy-2-phenethyl-benzofuran-4-carboxylic acid (3-5-dichloropyridin-4-yl)-amide, 5-(2-butyl-7-methoxy-benzofuran-4-yl)-tetrahydropyrimidin-2-one, phenyldihydrobenzofuranes, 4-substituted benzofuranes and substituted furans.

23. The method of claim 3, wherein the Type IV phosphodiesterase inhibitor is a naphthalene derivative.

24. The method of claim 23, wherein the naphthalene derivative is T 440.

25. The method of claim 3, wherein the Type IV phosphodiesterase inhibitor is a purine derivative.

26. The method of claim 25, wherein the purine derivative is V-112294A.

27. The method of claim 3, wherein the Type IV phosphodiesterase inhibitor is a cyclohexane carboxylic acid.

28. The method of claim 27, wherein the cyclohexane carboxylic acid is ariflo.

29. The method of claim 3, wherein the Type IV phosphodiesterase inhibitor is a benzamide.

30. The method of claim 29, wherein the benzamide is piclamilast.

31. The method of claim 3, wherein the Type IV phosphodiesterase inhibitor is a benzothiophene.

32. The method of claim 31, wherein the benzothiophene is tibenelast.

33. The method of claim 2, wherein the Type IV phosphodiesterase inhibitor is a pyridopyridazinone.

34. The method of claim 33, wherein the pyridopyridazinone has the structural formula

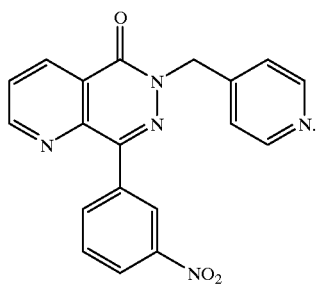

35. The method of claim 3, wherein the Type IV phosphodiesterase inhibitor is an imidazolidinone.

36. The method of claim 34, wherein the imidazolidinone has the structural formula

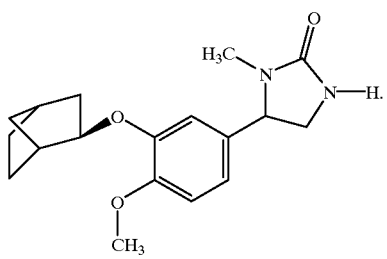

37. The method of claim 1, wherein the individual is given a daily dose of phosphodiesterase inhibitor in the range of approximately 0.01 to 500 mg.

38. The method of claim 1, wherein the phosphodiesterase inhibitor is administered one to four times in a twenty-four hour period.

39. The method of claim 1, wherein the erectile dysfunction is vasculogenic impotence.

40. The method of claim 1, wherein the formulation comprises a unit dosage of the phosphodiesterase inhibitor.

41. The method of claim 1, wherein the Type IV phosphodiesterase inhibitor is co-administered with an additional active agent.

42. The method of claim 41, wherein the additional active agent is an additional phosphodiesterase inhibitor.

43. The method of claim 42, wherein the additional phosphodiesterase inhibitor is an additional Type IV phosphodiesterase inhibitor.

44. The method of claim 42, wherein the additional phosphodiesterase inhibitor is a Type III phosphodiesterase inhibitor.

45. The method of claim 42, wherein the additional phosphodiesterase inhibitor is a Type V phosphodiesterase inhibitor.

46. The method of claim 42, wherein the additional phosphodiesterase inhibitor is a nonspecific phosphodiesterase inhibitor.

47. The method of claim 41, wherein the additional active agent is selected from the group consisting of nitrovasodilators, alpha receptor blocking agents, ergot alkaloids, naturally occurring, semisynthetic and synthetic prostaglandins; vasoactive intestinal peptide; and combinations thereof.

48. The method of claim 47, wherein the additional active agent is a prostaglandin.

49. The method of claim 48, wherein the additional active agent is $PGE_1$.

50. The method of claim 1, wherein the formulation is administered transurethrally.

51. The method of claim 50, wherein the formulation comprises a urethral suppository.

52. The method of claim 1, wherein the formulation is administered by intracavernosal injection.

53. The method of claim 1, wherein the formulation is administered topically.

54. The method of claim 1, wherein the formulation is administered transdermally.

55. A pharmaceutical formulation for treating erectile dysfunction comprising a therapeutically effective amount of a Type IV phosphodiesterase inhibitor or a pharmaceutically acceptable salt, ester, amide or prodrug thereof, and a pharmaceutically acceptable carrier suitable for local drug administration.

56. The formulation of claim 55, wherein the therapeutically effective amount is a unit dosage.

57. The formulation of claim 55, wherein the pharmaceutically acceptable carrier is suitable for transurethral drug administration, and the formulation comprises a urethral dosage form.

58. The formulation of claim 57, wherein the urethral dosage form comprises a urethral suppository.

59. The formulation of claim 58, wherein the carrier is selected from the group consisting of polyethylene glycol and derivatives thereof.

60. The formulation of claim 55, comprising a sterile liquid composition and wherein the carrier is suitable for intracavernosal injection.

61. The formulation of claim 55, comprising a composition to be applied to a body surface, and wherein the carrier is suitable for topical or transdermal administration.

62. The formulation of claim 61, wherein the composition is an ointment, cream, gel or lotion.

63. The formulation of claim 55, wherein the Type IV phosphodiesterase inhibitor is selected from the group consisting of pyrrolidinones, quinazolinediones, xanthine derivatives, phenyl ethyl pyridines, tetrahydropyrimidones, diazepine derivatives, oxime carbamates, naphthyridinones, benzofurans, naphthalene derivatives, purine derivatives, imidazolidinones, cyclohexane carboxylic acids, benzamides, pyridopyridazinones, benzothiophenes, etazolate, S-(+)-glaucine, substituted phenyl compounds and substituted biphenyl compounds.

64. The formulation of claim 55, wherein the Type IV phosphodiesterase inhibitor is a pyrrolidinone.

65. The formulation of claim 64, wherein the pyrrolidinone is selected from the group consisting of rolipram, RO20-1724 and RS 33793.

66. The formulation of claim 55, wherein the Type IV phosphodiesterase inhibitor is a quinazolinedione.

67. The formulation of claim 66, wherein the quinazolinedione is selected from the group consisting of nitraquazone, CP-77059 and RS-25344.

68. The formulation of claim 55, wherein the Type IV phosphodiesterase inhibitor is a xanthine derivative.

69. The formulation of claim 68, wherein the xanthine derivative is selected from the group consisting of denbufylline, arofylline and BRL 61063.

70. The formulation of claim 55, wherein the Type IV phosphodiesterase inhibitor is a phenyl ethyl pyridine.

71. The formulation of claim 70, wherein the phenyl ethyl pyridine is CDP 840.

72. The formulation of claim 55, wherein the Type IV phosphodiesterase inhibitor is a tetrahydropyrimidone.

73. The formulation of claim 72, wherein the tetrahydropyrimidone is atizoram.

74. The formulation of claim 55, wherein the Type IV phosphodiesterase inhibitor is a diazepine derivative.

75. The formulation of claim 74, wherein the diazepine derivative is CI 1018.

76. The formulation of claim 55, wherein the Type IV phosphodiesterase inhibitor is an oxime carbamate.

77. The formulation of claim 76, wherein the oxime carbamate is filaminast.

78. The formulation of claim 55, wherein the Type IV phosphodiesterase inhibitor is a naphthyridinone.

79. The formulation of claim 78, wherein the naphthyridinone is RS 17597.

80. The formulation of claim 55, wherein the Type IV phosphodiesterase inhibitor is a benzofuran.

81. The formulation of claim 80, wherein the benzofuran is selected from the group consisting of 2-butyl-7-methoxy-benzofuran-4-carboxylic acid (3-5-dichloropyridin-4yl)-amide, 2-benzyl-7-methoxy-benzofuran-4-carboxylic acid (3-5-dichloropyridin-4-yl)-amide, 7-methoxy-2-phenethyl-benzofuran-4-carboxylic acid (3-5-dichloropyridin-4-yl)-amide, 5-(2-butyl-7-methoxy-benzofuran-4-yl)-tetrahydropyrimidin-2-one, phenyldihydrobenzofuranes, 4-substituted benzofuranes and substituted furans.

82. The formulation of claim 55, wherein the Type IV phosphodiesterase inhibitor is a naphthalene derivative.

83. The formulation of claim 82, wherein the naphthalene derivative is T 440.

84. The formulation of claim 55, wherein the Type IV phosphodiesterase inhibitor is a purine derivative.

85. The formulation of claim 84, wherein the purine derivative is V-12294A.

86. The formulation of claim 55, wherein the Type IV phosphodiesterase inhibitor is a cyclohexane carboxylic acid.

87. The formulation of claim 86, wherein the cyclohexane carboxylic acid is ariflo.

88. The formulation of claim 55, wherein the Type IV phosphodiesterase inhibitor is a benzamide.

89. The formulation of claim 88, wherein the benzamide is piclamilast.

90. The formulation of claim 55, wherein the Type IV phosphodiesterase inhibitor is a benzothiophene.

91. The formulation of claim 90, wherein the benzothiophene is tibenelast.

92. The formulation of claim 55, wherein the Type IV phosphodiesterase inhibitor is a pyridopyridazinone.

93. The formulation of claim 92, wherein the pyridopyridazinone has the structural formula

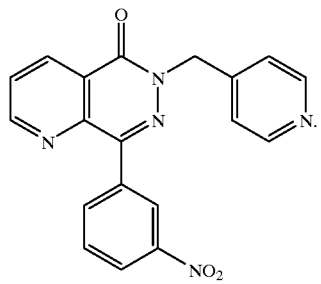

94. The formulation of claim 55, wherein the Type IV phosphodiesterase inhibitor is an imidazolidinone.

95. The formulation of claim 94, wherein the imidazolidinone has the structural formula

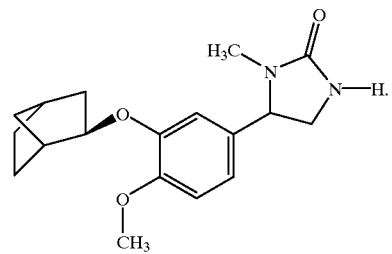

96. The formulation of claim 55, further including an additional active agent.

97. The formulation of claim 96, wherein the additional active agent is an additional phosphodiesterase inhibitor.

98. The formulation of claim 97, wherein the additional active agent is an additional Type IV phosphodiesterase inhibitor.

99. The formulation of claim 97, wherein the additional active agent is a Type III phosphodiesterase inhibitor.

100. The formulation of claim 97, wherein the additional active agent is a Type V phosphodiesterase inhibitor.

101. The formulation of claim 96, wherein the additional active agent is selected from the group consisting of nitrovasodilators, alpha receptor blocking agents, ergot alkaloids, naturally occurring, semisynthetic and synthetic prostaglandins; vasoactive intestinal peptide; and combinations thereof.

102. The formulation of claim 101, wherein the additional active agent is a prostaglandin.

103. The formulation of claim 102, wherein the additional active agent is $PGE_1$.

104. A kit for treating erectile dysfunction, comprising: a pharmaceutical formulation containing a Type IV phosphodiesterase inhibitor or a pharmaceutically acceptable salt, ester, amide or prodrug thereof; a means for locally administering the formulation; a container for housing the formulation and drug delivery means; and instructions for using the drug delivery means to administer the formulation within the context of a dosing regimen effective to treat erectile dysfunction.

105. The kit of claim 104, wherein the formulation comprises a urethral dosage form, and the means for administering the agent is a transurethral drug delivery device.

106. The kit of claim 105, further including a flexible, adjustable venous flow control (VFC) device and instructions for using the VFC device.

* * * * *